US00PP32008P2

(12) United States Plant Patent
Van Swieten

(10) Patent No.: US PP32,008 P2
(45) Date of Patent: Jul. 21, 2020

(54) ***PHALAENOPSIS* ORCHID PLANT NAMED 'PHALVILMYK'**

(50) Latin Name: ***Phalaenopsis* hybrid**
Varietal Denomination: PHALVILMYK

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,736

(22) Filed: May 30, 2019

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named 'PHALVILMYK'; QZ PBR 20171134, filed Apr. 25, 2017.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALVILMYK', particularly characterized by having red flowers with slightly greenish-yellow apexes and centers and red-purple lips, 1 to 3 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALVILMYK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALVILMYK'.

The new *Phalaenopsis* plant is a product of a planned breeding program conducted by the inventor in Bleiswijk, the Netherlands. The objective of this breeding program was to create a new *Phalaenopsis* plant with numerous attractive red flowers with slightly yellow-green apexes and centers and red-purple lips, suitable for potted plant production.

The new *Phalaenopsis* plant 'PHALVILMYK' is a result of cross-pollination made by the inventor in August 2006 in Bleiswijk, the Netherlands, of the proprietary female, or seed parent, *Phalaenopsis* hybrid '01-1434' (unpatented) with the proprietary male, or pollen parent, *Phalaenopsis* hybrid '21864-015' (unpatented).

The new *Phalaenopsis* was selected by the inventor as a single plant within the progeny of the stated cross-pollination in a controlled greenhouse in Bleiswijk, the Netherlands, in August 2009. Asexual reproduction of the new *Phalaenopsis* plant by meristem tissue culture since 2012 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Apr. 25, 2017, by Applicant who obtained the subject matter disclosed directly from the Inventor. 'PHALVILMYK' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALVILMYK' as a new and distinct variety of *Phalaenopsis* plant:

1) Red flowers with slightly greenish-yellow apexes and centers and red-purple lips;
2) 1 to 3 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in March 2019. Colors in the photographs may differ from the color values cited in the detailed botanical description, which accurately describe the actual colors of the new variety.

DESCRIPTION OF THE NEW VARIETY

Figure 1:
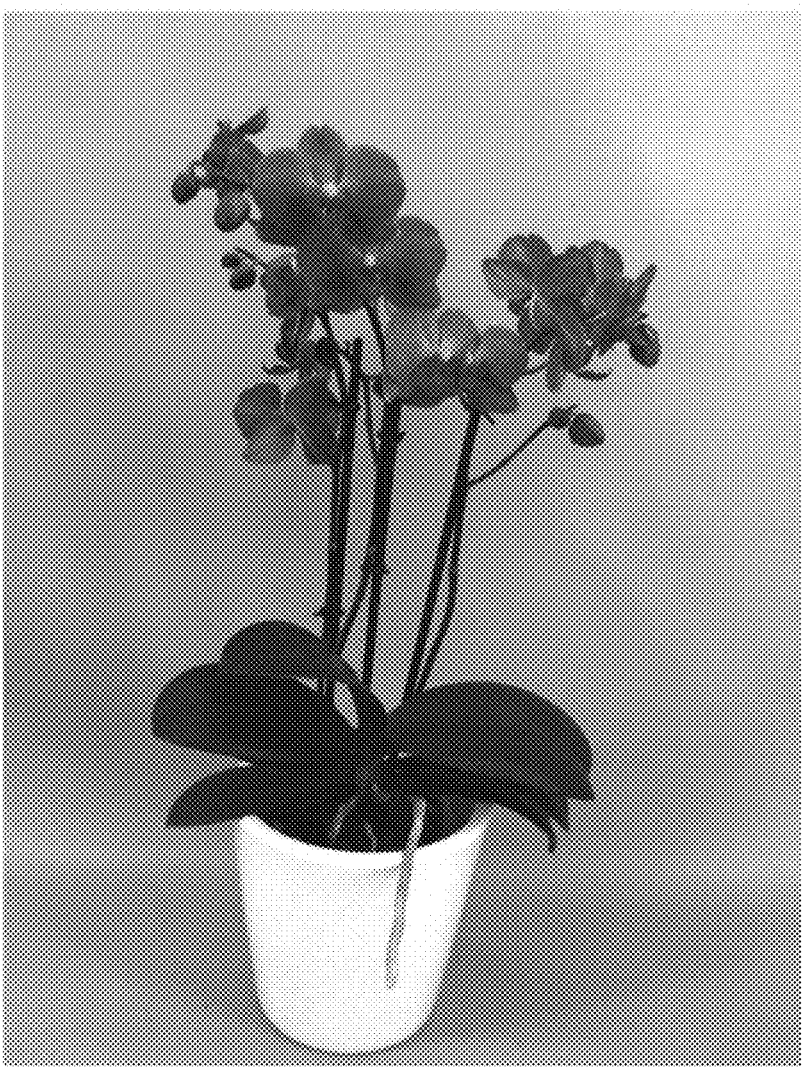
FIG. 1 shows the overall plant habit, including blooms, buds, and foliage of 'PHALVILMYK'.
Figure 2:
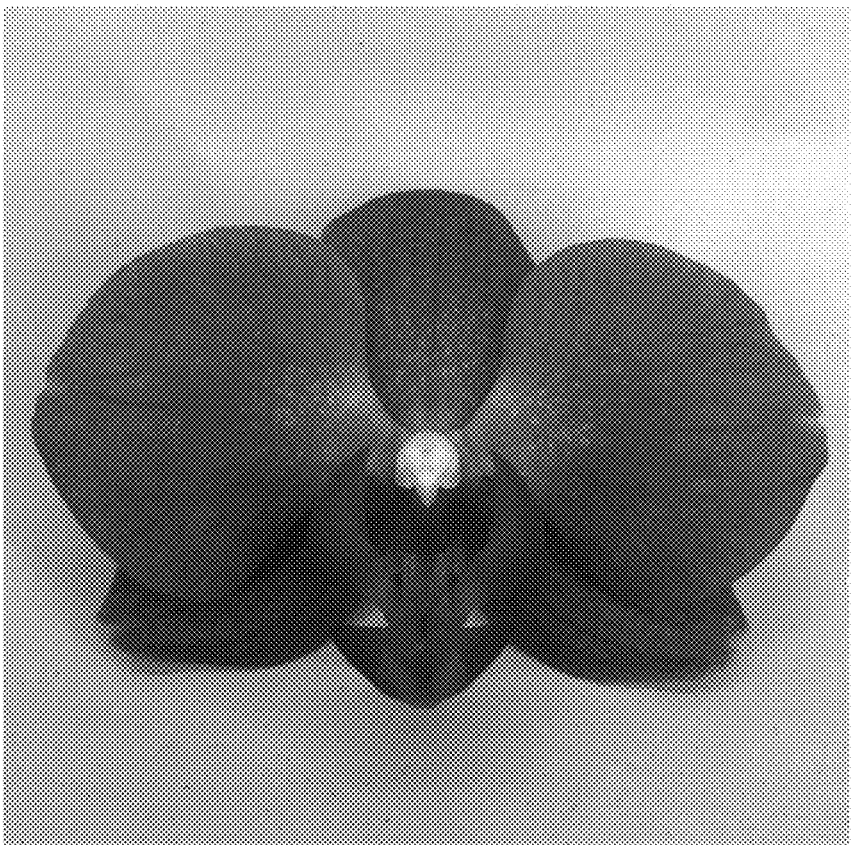
FIG. 2 shows a close-up of a flower of 'PHALVILMYK'.
Figure 3:
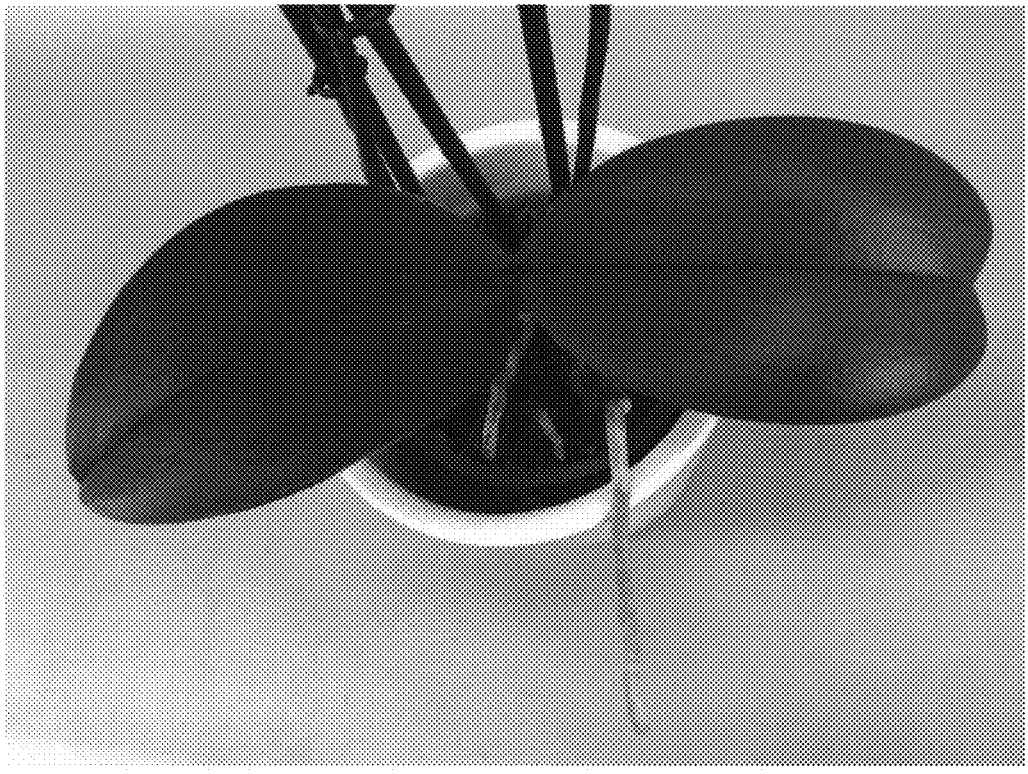
FIG. 3 shows an overhead view of the leaves of 'PHALVILMYK'.

The following detailed description sets forth the distinctive characteristics of 'PHALVILMYK'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in March 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALVILMYK'.

Parentage:

*Female parent*.—*Phalaenopsis* cultivar '01-1434' (unpatented).

*Male parent*.—*Phalaenopsis* cultivar '21864-015' (unpatented).

Propagation:

*Type*.—Meristem tissue culture.

Roots:

*Root description*.—Greyed-green (between RHS 190B and 190C) colored roots with branching lateral roots having yellow-green (RHS 145A) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme or panicle inflorescence.

*Height (from soil level to top of inflorescence)*.—Approximately 34.0 cm to 39.0 cm.

*Width (measured from leaf tips)*.—About 25.0 cm to 27.0 cm.

*Vigor*.—Moderate.

Leaves:

*Mature leaves*.—Quantity per plant: 8 to 10 leaves are produced before flowering. Length (fully expanded): 13.0 cm to 15.0 cm. Width: 7.0 cm to 8.0 cm. Shape: Oblong. Base shape: Slightly to moderately elongated. Apex: Obtuse unequal. Leaf blade angle with the petiole (measured from the horizontal position): Between 20 degrees and 35 degrees. Leaf margin: Entire. Color: Upper surface: RHS 147A. Lower surface: RHS 147B. Texture (both upper and lower surfaces): Rough. Thickness: 2.0 mm to 3.0 mm. Variegation: Absent. Venation: Pattern: Parallel. Color of the midvein: Upper surface: RHS 147A. Lower surface: RHS 146B.

Peduncle:

*Quantity per plant*.—1 to 3.

*Number of flowers per peduncle*.—8 to 12.

*Length*.—34.0 cm to 39.0 cm.

*Diameter*.—3.8 mm to 4.3 mm.

*Strength*.—Strong.

*Aspect*.—Upright to slightly pendant.

*Texture*.—Smooth.

*Color*.—Mix of green (mix of RHS 146B and 146C) and brown (RHS N200A) mostly at the base.

*Internode length*.—4.0 cm to 5.0 cm.

Inflorescence description:

*Appearance*.—Upright to slightly pendant, raceme or panicle inflorescence with bilaterally symmetrical flowers that open in succession beginning with the lowermost flower.

*Number of inflorescences*.—1 to 3.

*Inflorescence size*.—Height (from base to tip): 170.0 mm to 200.0 mm.

*Flowering time*.—First flowers can be expected 10 to 11 months after planting in a 12-cm pot.

*Flower*.—Height: 58.0 mm to 63.0 mm. Diameter: 67.0 mm to 72.0 mm. Depth of lip: 19.0 mm to 21.0 mm.

*Flower longevity*.—On the plant: 16 to 21 weeks.

*Fragrance*.—Absent.

*Flower bud*.—Average size: Medium to large. Length: 21.0 mm to 23.0 mm. Width: 18.0 mm to 20.0 mm. Shape: Egg shaped. Color: Yellow-green (RHS 146D) with a touch of purplish-red (RHS N77B).

*Petals*.—Arrangement: Open/free. Shape: Semi-circular. Apex: Emarginated asymmetric. Margin: Slightly wavy. Length (from base to tip): 29.0 mm to 31.0 mm. Width: 35.0 mm to 37.0 mm. Position of the broadest part of the petal: At the base. Color (when fully opened): Upper surface: Basic color: Red (RHS 185B). Over color: Slightly light yellow-green (RHS 145C) at the apex and the base; reddish-purple (RHS N78B) at the base. Lower surface: Basic color: Red (RHS 188C and 186A). Over color: Light green (RHS 145C to 145D) in the middle.

*Dorsal sepal*.—Shape: Elliptic. Apex: Emarginated symmetric. Margin: Entire. Length (from base to tip): 37.0 mm to 39.0 mm. Width: 24.0 mm to 26.0 mm. Color (when fully opened): Upper surface: Basic color: Red (RHS 184B). Over color: Light yellow-green small dots and apex (RHS 145C). Lower surface: Basic color: Red (RHS 185C). Over color: Yellow-green (RHS 145A to 145B) in the middle.

*Lateral sepals*.—Shape: Ovate. Apex: Obtuse asymmetric. Margin: Entire. Length (from base to tip): 34.0 mm to 36.0 mm. Width: 25.0 mm to 27.0 mm. Color (when fully opened): Upper surface: Basic color: Reddish-purple (RHS 184B). Over color: Light yellow-green (RHS 145C) at the base and apex. Lower surface: Basic color: Red (RHS 185C). Over color: Light yellow-green (RHS 145B to 145C) in the middle.

*Labellum* (*lip*).—Whiskers: Present. Length of whiskers: 5.0 mm to 7.0 mm. Color of whiskers: Dark purplish-red (RHS N79C) with very small white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 14.0 mm to 16.0 mm. Width: 7.0 mm to 9.0 mm. Color: Slightly yellow (RHS 6C) at the base; dark red (RHS 59A) on one side; purplish-red (RHS N78A) toward other side.

*Apical lobe*.—Shape: Rhombic. Margin: Entire. Length: 15.0 mm to 17.0 mm. Width: 14.0 mm to 16.0 mm. Color: Slightly red (RHS 180A) at the base; dark red (RHS 59A) and purplish-red (RHS 59B) toward whiskers. Bump and ridge: Present.

*Callus*.—Average size: Small to medium. Height: 5.0 mm to 6.0 mm. Length: 4.0 mm to 5.0 mm. Width: 4.0 mm to 5.0 mm. Color: Yellow (RHS 7A); flecked (RHS 180A).

Reproductive organs:

*Column*.—Length: 8.0 mm to 10.0 mm. Diameter: 4.6 mm to 5.0 mm. Color: Red-purple (RHS N78B to N78C).

*Pollinia*.—Quantity: 2. Diameter: 0.7 mm to 0.9 mm. Color: Orange-yellow (RHS 23A).

*Ovary*.—Length: 8.0 mm to 10.0 mm. Diameter: 2.0 mm to 2.2 mm. Color: Light yellow-green (RHS 145B) and very light yellow-green (RHS 145D) toward the flower.

*Pedicel*.—Length: 29.0 mm to 31.0 mm. Diameter: 2.2 mm to 2.4 mm. Color: Yellow-green (RHS 146D) at the base and light yellow-green (RHS 145B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALVILMYK' differs from female parent plant '01-1434' (unpatented) in that 'PHALVILMYK' has rhombic apical lobes, weakly spatulate lateral lobes, and flowers with a basic color of red, whereas '01-1434' has triangular apical lobes, spatulate lateral lobes, and flowers with a basic color of reddish-purple. Additionally, 'PHALVILMYK' has smaller flowers and narrower petals than '01-1434'.

'PHALVILMYK' differs from male parent plant '21864-015' (unpatented) in that 'PHALVILMYK' has weakly spatulate lateral lobes, red-purple columns, and flowers with a basic color of red, whereas '21864-015' has oblong lateral lobes, white columns, and flowers with a basic color of greenish-yellow. Additionally, 'PHALVILMYK' has larger flowers and wider petals than '21864-015'.

'PHALVILMYK' is most similar to the commercial *Phalaenopsis* plants named 'PHALIFQUDI' (U.S. Plant Pat. No. 26,831) and 'PHALADADEL' (unpatented). 'PHALVILMYK' differs from the commercial variety 'PHALIFQUDI' in that 'PHALVILMYK' weakly spatulate lateral lobes, whereas 'PHALIFQUDI' has spatulate lateral lobes. Additionally, 'PHALVILMYK' has smaller flowers, narrower petals, and shorter whiskers than 'PHALIFQUDI'.

'PHALVILMYK' differs from the commercial variety 'PHALADADEL' in that 'PHALVILMYK' has emarginated petal apexes, whereas 'PHALADADEL' has obtuse petal apexes. Additionally, 'PHALVILMYK' has smaller flowers and narrower petals than 'PHALADADEL'.

I claim:

1. A new and distinct variety of *Phalaenopsis* plant named 'PHALVILMYK', substantially as described and illustrated herein.

* * * * *